United States Patent [19]
Atkinson

[11] Patent Number: 5,599,333
[45] Date of Patent: Feb. 4, 1997

[54] SUCTION ADAPTER

[75] Inventor: Robert W. Atkinson, Dover, Ohio

[73] Assignee: Zimmer, Inc., Warsaw, Ind.

[21] Appl. No.: 366,151

[22] Filed: Dec. 29, 1994

[51] Int. Cl.⁶ .................................................. A61M 1/00
[52] U.S. Cl. ........................ 604/326; 604/317; 604/320; 604/323; 604/902; 604/905; 128/912
[58] Field of Search .................................. 604/19, 27, 35, 604/45, 48, 93, 317–324, 326, 902, 905; 128/912; 137/605; 261/78.2

[56] References Cited

U.S. PATENT DOCUMENTS

| | | | |
|---|---|---|---|
| 3,319,628 | 5/1967 | Halligan | 128/276 |
| 3,959,234 | 7/1971 | Jackson | 128/276 |
| 4,211,240 | 7/1980 | Gallagher | 128/725 |
| 4,287,889 | 9/1981 | Stupar | 128/276 |
| 4,356,823 | 11/1982 | Jackson | 128/276 |
| 4,534,542 | 8/1985 | Russo | 604/48 |
| 4,699,138 | 10/1987 | Behrstock | 604/902 |
| 4,966,584 | 10/1990 | Nguyen | 604/119 |
| 5,195,952 | 3/1993 | Solnit et al. | 604/19 |
| 5,328,456 | 7/1994 | Horiguchi et al. | 604/22 |
| 5,328,478 | 7/1994 | McVay | 604/147 |
| 5,335,655 | 8/1994 | Kee | 128/207.16 |
| 5,336,169 | 8/1994 | Divilio et al. | 604/22 |

Primary Examiner—David Isabella
Assistant Examiner—Dennis Ruhl
Attorney, Agent, or Firm—Cary R. Reeves

[57] ABSTRACT

A suction adapter couples a fluid drain tube to a suction canister for fluid collection while maintaining the drain tube at atmospheric pressure for optimal draining flow rate. The suction adapter further allows the surgeon to easily apply suction to the drain tube when he desires to increase the flow rate through the drain tube and to just as easily return the drain tube to atmospheric pressure. The suction adapter does not spill and is muffled to reduce noise. The suction adapter comprises a housing defining an interior space. The housing has a suction port in communication with the interior space for connection to a suction source and a fluid port in communication with the interior space for connection to a fluid drain tube. The housing also has a ventilation port formed in the housing to allow atmospheric air into the interior space. The ventilation port communicates with a ventilation tube located in the interior space, the ventilation tube having a ventilation hole. In a preferred embodiment, a sound dampening porous foam is located within the interior space around the ventilation tube.

10 Claims, 3 Drawing Sheets

SUCTION ADAPTER

BACKGROUND OF THE INVENTION

The present invention relates to fluid systems for communicating fluid to and from a patient to facilitate a surgical procedure. More particularly, the present invention relates to a suction adapter for connecting the drain of a fluid system to a suction source.

Various surgical procedures used to treat the human body require communicating fluid away from the body. For example, in endoscopic procedures used to treat a uterus or a knee fluid is communicated to the surgical site in order to distend the surrounding tissues so as to facilitate visualization of and access to the surgical site. An exemplary system for distending such a surgical site is taught by U.S. Pat. No. 5,152,746. The fluid communicated to the surgical site is subsequently communicated away from the surgical site through a drain tube. The fluid is typically collected for disposal and measurement in a suitable container such as a bucket as shown in FIG. 1. The collection chamber is usually open to atmospheric pressure because if the pressure in the collection chamber is higher than atmospheric pressure it will impede the flow through the drain tube. On the other hand if the pressure in the collection chamber is below atmospheric pressure, the fluid may drain away from the surgical site too quickly and reduce the distension pressure at the surgical site. However, an occasional and controlled brief reduction in the pressure in the drain tube can be helpful to momentarily increase the flow away from the surgical site to clear debris or temporarily reduce the amount of distension. The open containers previously used do not facilitate such momentary suction on the drain tube. Furthermore, the prior art open containers are easily tipped and spilled in the crowded operating room environment.

Often, in the course of a single surgical procedure, much more fluid is used than can be collected in a single collection container. In such a case it is desirable to connect additional containers to the first container. The additional containers are connected to a suction source so that they will draw fluid away from the first container thus allowing the first container to receive more fluid without overflowing.

SUMMARY OF THE INVENTION

The present invention provides a suction adapter for coupling a fluid drain tube to a suction canister for fluid collection while maintaining the drain tube at atmospheric pressure for optimal draining flow rate. The suction adapter further allows the surgeon to easily apply suction to the drain tube when he desires to increase the flow rate through the drain tube and to just as easily return the drain tube to atmospheric pressure. The suction adapter provides a connection that will not allow drain fluid to spill into the operating room environment. Finally, the suction adapter of the present invention is muffled to reduce noise.

The suction adapter of the present invention comprises a housing defining an interior space. The housing has a suction port in communication with the interior space for connection to a suction source and a fluid port in communication with the interior space for connection to a fluid drain tube. The housing also has a ventilation port formed in the housing to allow atmospheric air into the interior space. The ventilation port communicates with a ventilation tube located in the interior space, the ventilation tube having a ventilation hole. In a preferred embodiment, a sound dampening porous foam is located within the interior space around the ventilation tube.

DETAILED DESCRIPTION OF THE INVENTION

Figure 1:
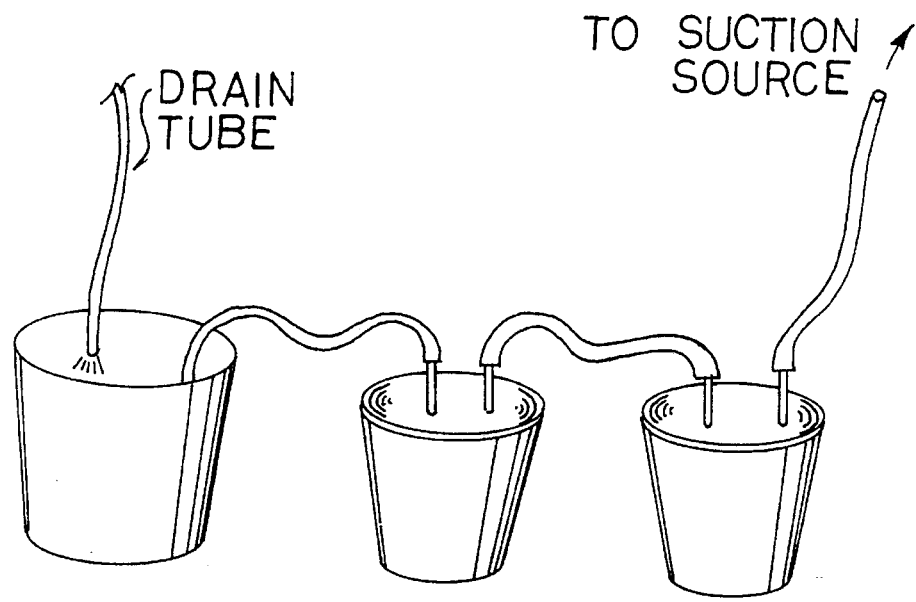
FIG. 1 shows a prior art fluid collection arrangement.
Figure 2:
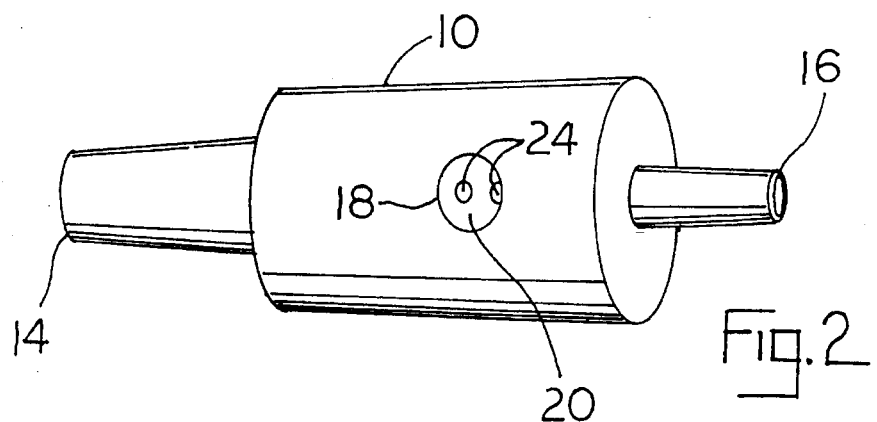
FIG. 2 is a perspective view of the suction adapter of the present invention.
Figure 3:
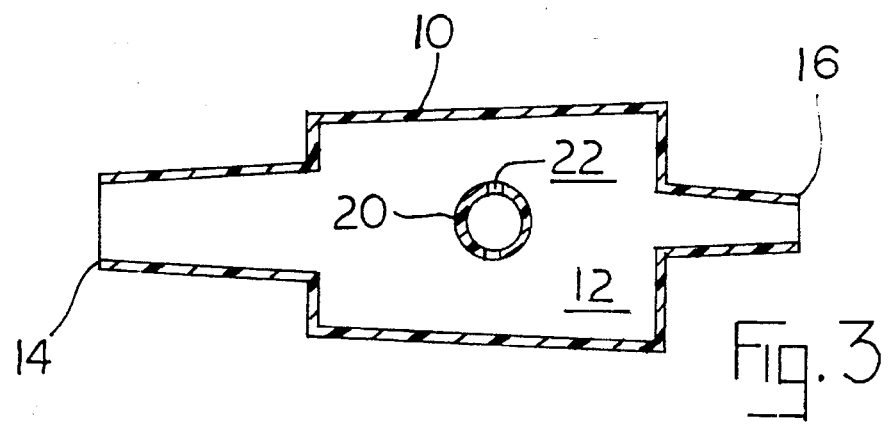
FIG. 3 is a side sectional view of the suction adapter of the present invention.
Figure 4:
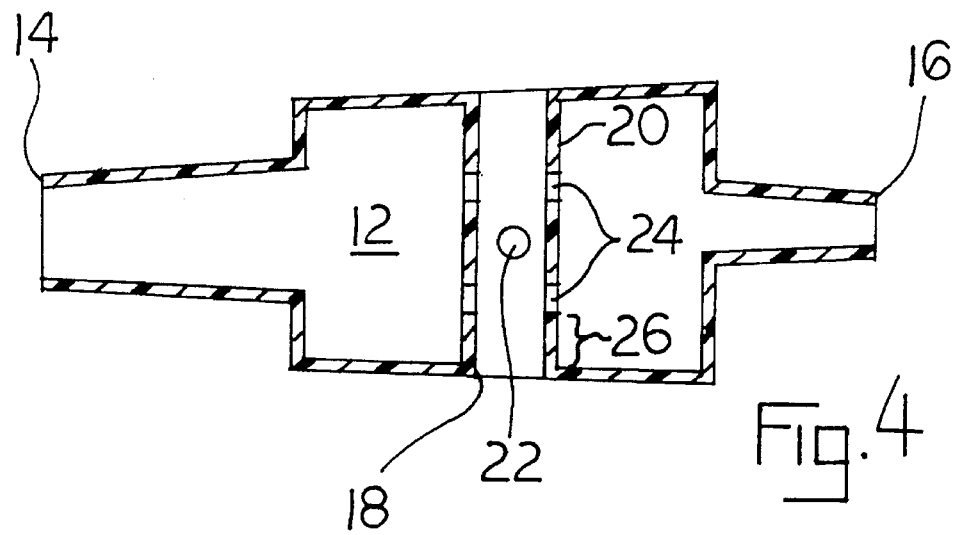
FIG. 4 is a side sectional view of the suction adapter of the present invention rotated 90 degrees from the view of FIG. 3.

Referring to FIGS. 2 through 4, the suction adapter of the present invention comprises a housing 10 having a wall defining an interior space 12. The housing 10 is fluid tight such that the interior space 12 is closed except for certain ports communicating with the interior space 12. The housing 10 has a suction port 14 in communication with the interior space 12 for connection to a suction source and a fluid port 16 in communication with the interior space 12 for connection to a fluid drain tube. The housing 10 also has a ventilation port 18 in communication with the interior space 12 to allow atmospheric air into the interior space 12. The ventilation port 18 communicates with a ventilation tube 20 located in the interior space 12. The ventilation tube 20 is connected to the housing 10 and extends into the interior space 12. The ventilation tube 20 also has a ventilation hole 22 through which it communicates with the interior space 12. Preferably the housing 10 contains opposed ventilation ports and the ventilation tube 20, in the form of a cylindrical tube having a longitudinal side wall, connects the ventilation ports to one another as shown in FIG. 4. Furthermore, the ventilation tube 20 preferably contains a plurality of ventilation holes 22 and 24 located in the longitudinal side wall. The ventilation holes 24 located nearest to the ventilation ports are preferably spaced a distance 26 from the housing wall. The ventilation tube 20 prevents drain fluid flowing through the suction adapter from spilling from the ventilation port 18. The suction adapter is preferably in the form of a cylinder or tapering cylinder with a maximum diameter less than three inches. More preferably the maximum diameter is less than one inch. Also the suction adapter is preferably constructed of a lightweight material such as plastic. The small size and light weight of the suction adapter allow it to be connected to a short drain tube so that the suction adapter hangs above the floor near the patient and surgeon without undue weight on the fluid tubing and without being in the way of the surgeon or patient. With the suction adapter so located it is easily accessible to the surgeon.

Figure 5:
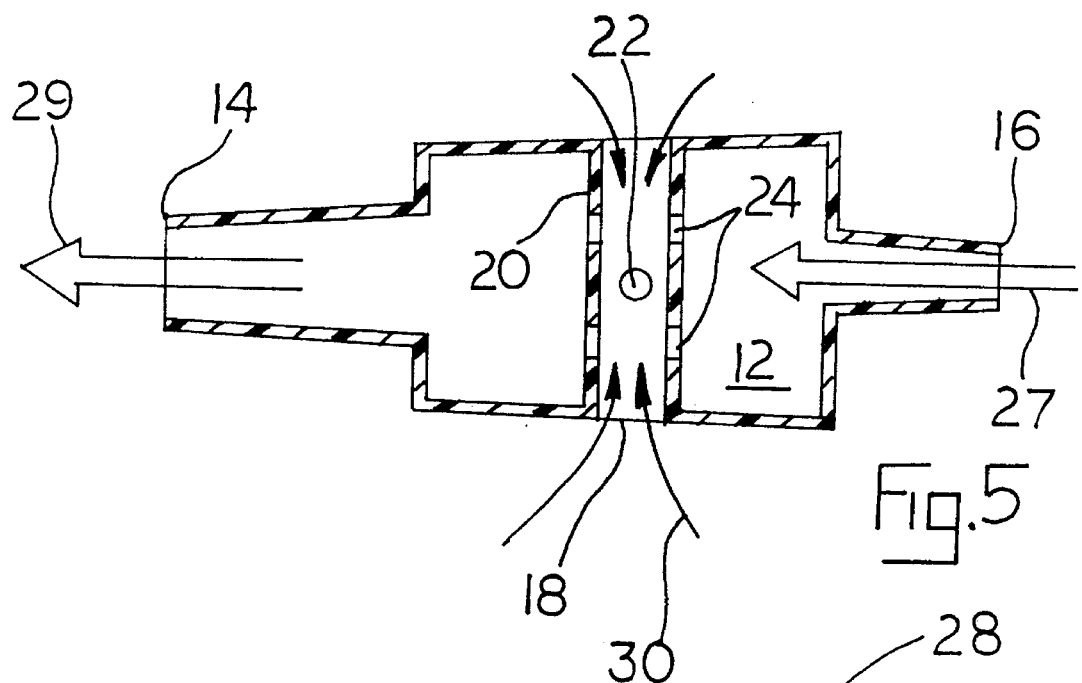
FIG. 5 is a view similar to FIG. 4 but showing the flow of drain fluid and air through the suction adapter.
Figure 6:
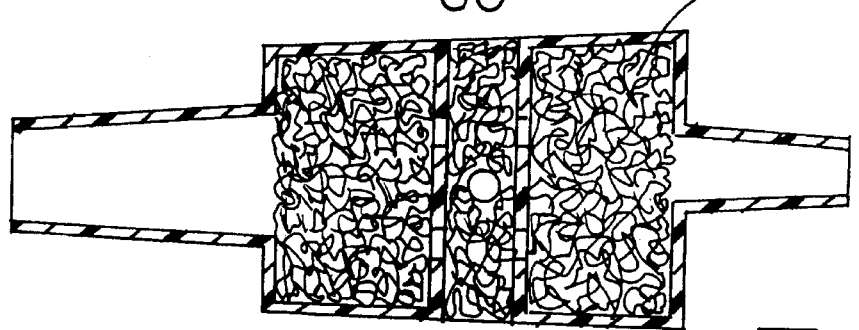
FIG. 6 is a view similar to FIG. 4 but showing the sound dampening foam of an embodiment of the present invention.

In use, drain fluid enters the interior space 12 through the fluid port 16 in the direction of arrow 27 as shown in FIG. 5. Air and drain fluid are evacuated from the interior space 12 through the suction port 14 in the direction of arrow 29. The suction provided by a typical suction canister is sufficient to remove drain fluid from the interior space 12 faster than the rate at which the drain tube discharges drain fluid into the interior space 12. However, in the present invention, undesirable suction is not applied to the drain tube because air is vented in the direction of arrows 30 into the interior space 12 through the ventilation port 18 and ventilation holes 22 and 24. As drain fluid moves through interior space 12, it travels around the ventilation tube 20. As long as the suction applied to the suction port 14 is sufficient to remove the drain fluid at a rate equal to or greater than the rate at which it enters the interior space 20, drain fluid will not leak from the suction adapter regardless of the position of the suction adapter. For example, if the suction adapter is in the position shown in FIG. 4, drain fluid will travel around the ventilation tube 20 and will not leak from the ventilation holes 24 because of their spacing 26 from the housing 10. If the suction adapter is in the position shown in FIG. 3, drain fluid will travel under the ventilation tube 20. Furthermore, the small size of the ventilation holes 22 and 24 relative to the suction port 14 results in air rushing through the ventilation holes 22 and 24 and the presence of this rushing air also prevents drain fluid from spilling through the ventilation holes. On the other hand, the vent holes are sufficiently large to allow enough air into the interior space to prevent the pressure in the fluid port from dropping significantly below atmospheric pressure. It has been found for example that a suction port diameter of 0.200 inches, a fluid port diameter of 0.145 inches, a ventilation tube diameter of 0.190 inches and four to ten ventilation holes having a diameter of 0.100 inches provide the desired results of no leakage and no suction on the fluid port.

Figure 7:
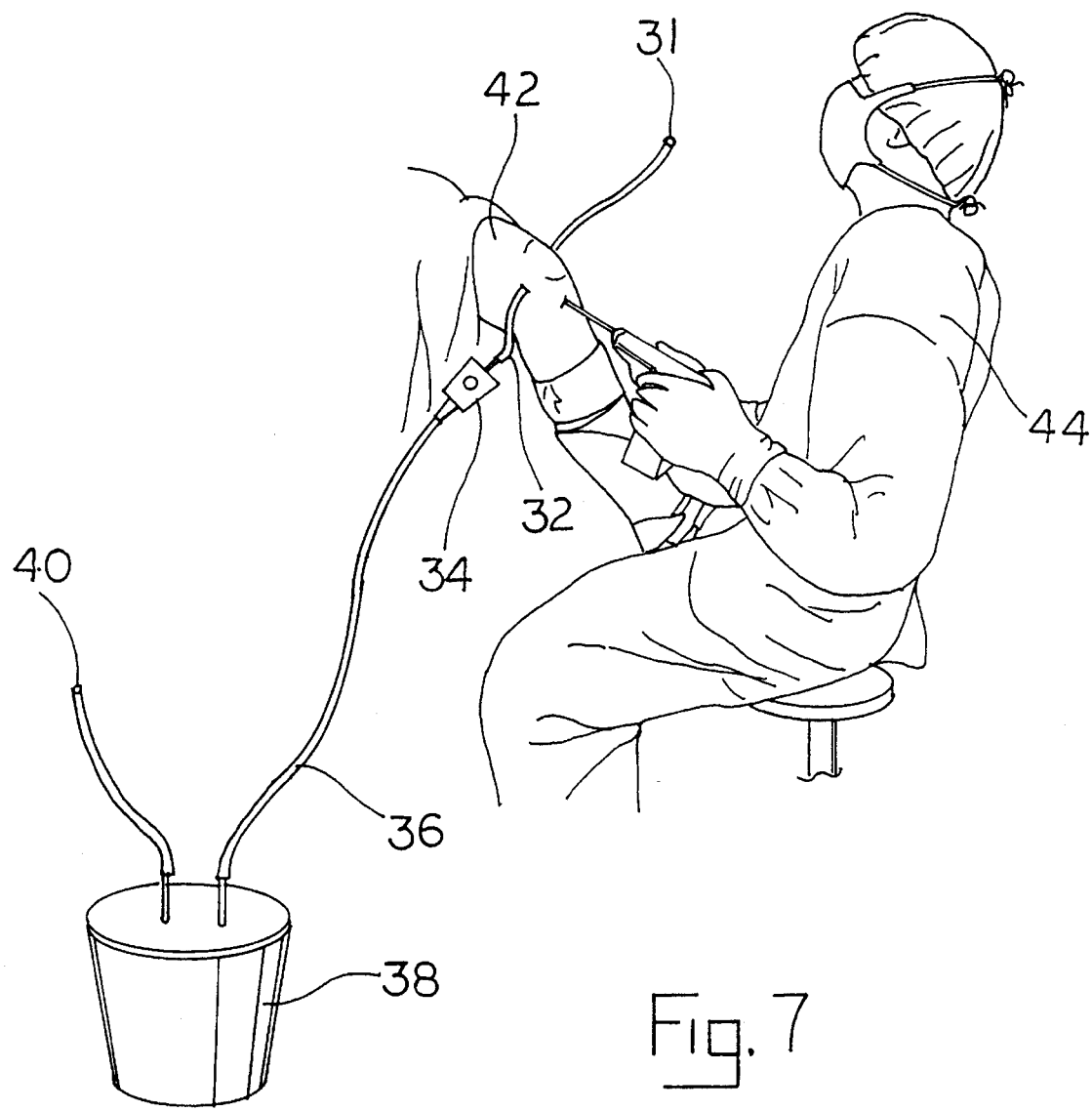
FIG. 7 shows the operating environment with the suction adapter of the present invention in use.

If the surgeon desires to apply suction to the drain tube, for example to clear debris from the surgical site more quickly, he need only cover the ventilation port 18 with his finger. This will prevent air from venting into the interior space and the suction will be applied directly to the fluid port to increase flow through the drain tube. Typically, the surgeon would grasp the suction adapter and cover and uncover the ventilation port 18 quickly to produce a pulse of suction in the drain tube. The small size and light weight of the suction adapter facilitate its being positioned near the surgeon so that it is easily accessible to him. Its small size also facilitates the surgeon grasping the suction adapter in his fingers and covering the ventilation port 18, or, in the embodiment with opposed ventilation ports, covering the ventilation ports with his thumb and first finger. FIG. 7 shows how a suction adapter according to the present invention would be situated within the operating environment. A fluid supply tube 31 supplies fluid to the surgical site. A drain tube 32 conducts drain fluid away from the surgical site. The suction adapter 34 connects the drain tube to a suction tube 36 leading to a suction canister 38. The suction canister is connected to a suction source by suction source tube 40. During surgery, the suction adapter 34 is positioned in close proximity to the patient 42 and surgeon 44, preferably it is suspended within easy reach of the surgeon. However, due to its small size and weight it does not create an obstruction for the surgeon 44. Therefore, in addition to being spill proof, the suction adapter 34 is positionable within easy reach of the surgeon 44 so that he can block the ventilation ports should he desire to increase the flow through the drain tube 32.

In a preferred embodiment, a sound dampening porous foam 28 is located within the interior space in order to reduce the noise resulting from air rushing through the ventilation holes 22 and 24 and mixing with the drain fluid in the interior space 12. The foam 28 is preferably a plastic foam easily permeated by the drain fluid and air. For example, an open cell polyurethane foam having 10 to 30 pores per square inch has been found to work well. It is most advantageous to fill the interior space 12 around the ventilation tube 20 as well as the inside of the ventilation tube 20 itself with the sound dampening foam.

It will be understood by those skilled in the art that the foregoing has described a preferred embodiment of the present invention and that variations in design and construction may be made to the preferred embodiment without departing from the spirit and scope of the invention defined by the appended claims.

What is claimed is:

1. A suction adapter usable by a user for connecting a surgical drain tube to a suction source, the suction adaptor comprising:

a housing defining an interior space;

a fluid port in the housing in fluid communication with the interior space;

a suction port in the housing in fluid communication with the interior space;

a first ventilation port in the housing;

a second ventilation port in the housing opposite to the first ventilation port, the size of the housing and the location of the ports being such that the ports can be readily occluded by fingers of one hand of said user when said user grasps the housing;

a ventilation tube extending through the interior space, the ventilation tube having first and second ends and a side wall, the ventilation tube being open at both the first and second ends, each of the ends communicating with a different one of the first and second ventilation ports, the ventilation tube containing a plurality of ventilation holes in its side wall through which it communicates with the interior space to allow the passage of air from the ventilation port through the ventilation tube and into the interior space.

2. A suction adapter for connecting a surgical drain tube to a suction source, the suction adapter comprising:

a housing defining an interior space;

a fluid port in the housing in fluid communication with the interior space;

a suction port in the housing in fluid communication with the interior space;

a first ventilation port in the housing;

a ventilation tube extending through the interior space, the ventilation tube having first and second ends and a side wall, the ventilation tube being open at at least one of the ends, the at least one open end of the ventilation tube being in fluid communication with the first ventilation port, the ventilation tube having at least one ventilation hole in fluid communication with the interior space to allow the passage of air from the ventilation port through the ventilation tube and into the interior space; and sound dampening foam located within the interior space and surrounding the ventilation tube.

3. A suction adapter for connecting a surgical drain tube to a suction source, the suction adapter comprising:

a housing defining an interior space;

a fluid port in the housing in fluid communication with the interior space;

a suction port in the housing in fluid communication with the interior space;

a first ventilation port in the housing;

a ventilation tube extending through the interior space, the ventilation tube having first and second ends and a side wall, the ventilation tube being open at at least one of the ends, the at least one open end of the ventilation tube being in fluid communication with the first ventilation port, the ventilation tube having at least one ventilation hole in fluid communication with the interior space to allow the passage of air from the ventilation port through the ventilation tube and into the interior space; and sound dampening foam located within the ventilation tube.

4. A suction adapter for connecting a surgical drain tube to a suction source, the suction adapter comprising:

a housing having a housing wall defining an interior space;

a fluid port in the housing in fluid communication with the interior space, the fluid port having a con_hector for connecting to said drain tube;

a suction port in the housing in fluid communication with the interior space, the suction port having a connector for connecting to said suction source;

a ventilation port in the housing in fluid communication with atmospheric air; and a ventilation tube in fluid communication with the ventilation port, the ventilation tube extending into the interior space, the ventilation tube having a ventilation hole in fluid communication with the interior space for communicating atmospheric air from the ventilation port into the interior space, the ventilation hole being located away from the housing wall for preventing fluid traveling along the housing wall from entering into the ventilation hole and leaking out of the ventilation port.

5. The suction adapter of claim 4 wherein the ventilation hole is smaller than the ventilation port.

6. The suction adapter of claim 4 wherein the housing has a longitudinal axis, the fluid port and suction port being located generally along the longitudinal axis.

7. The suction adapter of claim 6 wherein the ventilation tube is oriented approximately perpendicular to the longitudinal axis.

8. The suction adapter of claim 7 wherein a pair of ventilation ports are located in the housing, the ventilation tube passing through the interior space and being in fluid communication with both of the ventilation ports.

9. The suction adapter of claim 8 wherein the ventilation tube has a side wall and a plurality of ventilation holes are formed in the side wall, the ventilation holes being located away from the housing wall.

10. The suction adapter of claim 9 wherein the ventilation holes are each smaller than either of the ventilation ports.

* * * * *